(12) United States Patent
Ehlert et al.

(10) Patent No.: US 10,259,165 B2
(45) Date of Patent: Apr. 16, 2019

(54) APPARATUS FOR FABRICATING AN ELASTIC NONWOVEN MATERIAL

(71) Applicant: Aurizon Ultrasonics, LLC, Kimberly, WI (US)

(72) Inventors: Thomas David Ehlert, Neenah, WI (US); Patrick Sean McNichols, Hortonville, WI (US); Daniel James Sorensen, Neenah, WI (US); Casey John Morin, Appleton, WI (US); Brandon Leo Begrow, Hortonville, WI (US); Michael A Snyder, Hortonville, WI (US); Thomas Arthur Bett, Oshkosh, WI (US)

(73) Assignee: AURIZON ULTRASONICS, LLC, Kimberly, WI (US)

( * ) Notice: Subject to any disclaimer, the term of this patent is extended or adjusted under 35 U.S.C. 154(b) by 419 days.

(21) Appl. No.: 14/951,884

(22) Filed: Nov. 25, 2015

(65) Prior Publication Data

US 2016/0288407 A1    Oct. 6, 2016

Related U.S. Application Data

(60) Provisional application No. 62/247,056, filed on Oct. 27, 2015, provisional application No. 62/235,880, (Continued)

(51) Int. Cl.
*B32B 37/00*   (2006.01)
*B29C 65/08*   (2006.01)
(Continued)

(52) U.S. Cl.
CPC .......... *B29C 65/08* (2013.01); *B29C 65/087* (2013.01); *B29C 66/1122* (2013.01); (Continued)

(58) Field of Classification Search
CPC ... B29C 65/08; B29C 65/087; B29C 66/1122; B29C 66/433; B29C 66/7294; (Continued)

(56) References Cited

U.S. PATENT DOCUMENTS 3,993,532 A * 11/1976 McDonald ............ B29C 65/086
156/580.2
4,430,148 A    2/1984 Schaefer
(Continued)

FOREIGN PATENT DOCUMENTS

EP    1609582 A1    12/2005
EP    2412354 A1    2/2012
(Continued)

OTHER PUBLICATIONS

International Search Report and Written Opinion of related application PCT/US2016/24617 dated Jun. 30, 2016, 8 pp.
(Continued)

*Primary Examiner* — James D Sells
(74) *Attorney, Agent, or Firm* — Armstrong Teasdale LLP

(57) ABSTRACT

An apparatus for fabricating an elastic nonwoven material generally includes a rotary ultrasonic horn and a rotary anvil positionable in close proximity to the ultrasonic horn. The anvil has a face with a width and a circumferential axis. The face has a plurality of ridges each of which defines a plurality of interspaced lands and notches.

38 Claims, 10 Drawing Sheets

Related U.S. Application Data filed on Oct. 1, 2015, provisional application No. 62/141,496, filed on Apr. 1, 2015.

(51) Int. Cl.
*B29C 65/00* (2006.01)
*B29L 31/48* (2006.01)

(52) U.S. Cl.
CPC ........ *B29C 66/433* (2013.01); *B29C 66/7294* (2013.01); *B29C 66/7315* (2013.01); *B29C 66/8161* (2013.01); *B29C 66/81427* (2013.01); *B29C 66/81435* (2013.01); *B29C 66/81469* (2013.01); *B29C 66/8226* (2013.01); *B29C 66/8242* (2013.01); *B29C 66/8246* (2013.01); *B29C 66/83413* (2013.01); *B29C 66/8432* (2013.01); *B29C 66/876* (2013.01); *B29C 66/81465* (2013.01); *B29K 2995/0046* (2013.01); *B29L 2031/4878* (2013.01)

(58) Field of Classification Search
CPC .......... B29C 66/7315; B29C 66/81435; B29C 66/81469; B29C 66/8161; B29C 66/8226; B29C 66/8242; B29C 66/8246
USPC ...................................... 156/580.1
See application file for complete search history.

(56) References Cited

U.S. PATENT DOCUMENTS

| | | | |
|---|---|---|---|
| 5,733,411 A | 3/1998 | Bett | |
| 6,123,792 A | 9/2000 | Samida et al. | |
| 6,165,298 A * | 12/2000 | Samida | B29C 66/83411 |
| | | | 156/552 |
| 2003/0111157 A1 | 6/2003 | Ehlert et al. | |
| 2006/0144904 A1 | 7/2006 | Mlinar et al. | |

FOREIGN PATENT DOCUMENTS

| | | |
|---|---|---|
| JP | 2010115424 A | 5/2010 |
| JP | 2010220781 A | 10/2010 |
| JP | 2010220782 A | 10/2010 |
| JP | 2010220783 A | 10/2010 |
| WO | 2014010365 A1 | 1/2014 |
| WO | 2014200102 A1 | 12/2014 |

OTHER PUBLICATIONS

Partial EP Search Report for App. No. 16773958.0-1014/3277480 (PCT/US2016024617) dated Nov. 6, 2018; 15 pages.

* cited by examiner

APPARATUS FOR FABRICATING AN ELASTIC NONWOVEN MATERIAL

CROSS-REFERENCE TO RELATED APPLICATIONS

This application claims the benefit of U.S. Provisional Application No. 62/141,496 filed on Apr. 1, 2015, U.S. Provisional Application No. 62/235,880 filed on Oct. 1, 2015, and U.S. Provisional Application No. 62/247,056 filed on Oct. 27, 2015, all of which are incorporated by reference herein in their entirety.

BACKGROUND

The present invention relates generally to elastic materials and, more particularly, to an apparatus for fabricating an elastic nonwoven material.

Elastic nonwoven materials are utilized in a variety of articles including personal care articles (e.g., adult briefs, baby diapers, child/adult pull-on pants, contour fit hygiene products, etc.) and medical garments (e.g., masks, caps, gowns, footwear, etc.).

At least some conventional methods for fabricating elastic nonwoven materials include adhesively bonding elastic strands between layers of nonwoven fabric when the elastic strands are in tension. Once the elastic strands are permitted to contract, the elastic strands gather areas of the nonwoven fabric such that the nonwoven fabric functions with an elastic property. However, the durability of elastic nonwoven materials made by these conventional methods is less than desirable because the adhesive bonds are prone to creep, which can result in a loss of elasticity over time. Moreover, it can be overly expensive to fabricate elastic nonwoven materials using these conventional methods. It would be useful, therefore, to provide a system for fabricating a more durable elastic nonwoven material in a more cost effective manner.

SUMMARY

In one embodiment, an apparatus for fabricating an elastic nonwoven material generally comprises a rotary ultrasonic horn and a rotary anvil positionable in close proximity to the ultrasonic horn. The anvil has a face with a width and a circumferential axis. The face has a plurality of ridges each of which defines a plurality of interspaced lands and notches.

In another embodiment, an apparatus for fabricating an elastic nonwoven material generally comprises a horn module including a rotary ultrasonic horn mounted to a frame, and an anvil module including a rotary anvil mounted to a frame and positionable in close proximity to the ultrasonic horn. The apparatus also includes a camming device displaceably connecting the horn module and the anvil module to cyclically displace the horn module relative to the anvil module during a bonding operation of the apparatus.

In yet another embodiment, an apparatus for fabricating an elastic nonwoven material generally comprises a horn module including a rotary ultrasonic horn mounted to a frame, and an anvil module including a rotary anvil mounted to a frame and positionable in close proximity to the ultrasonic horn. The apparatus also includes a pinching device mounted to one of the frame of the horn module and the frame of the anvil module such that the pinching device is positionable to floatingly contact the anvil.

BRIEF DESCRIPTION

Corresponding reference characters indicate corresponding parts throughout the several views of the drawings.

DETAILED DESCRIPTION

Figure 1:
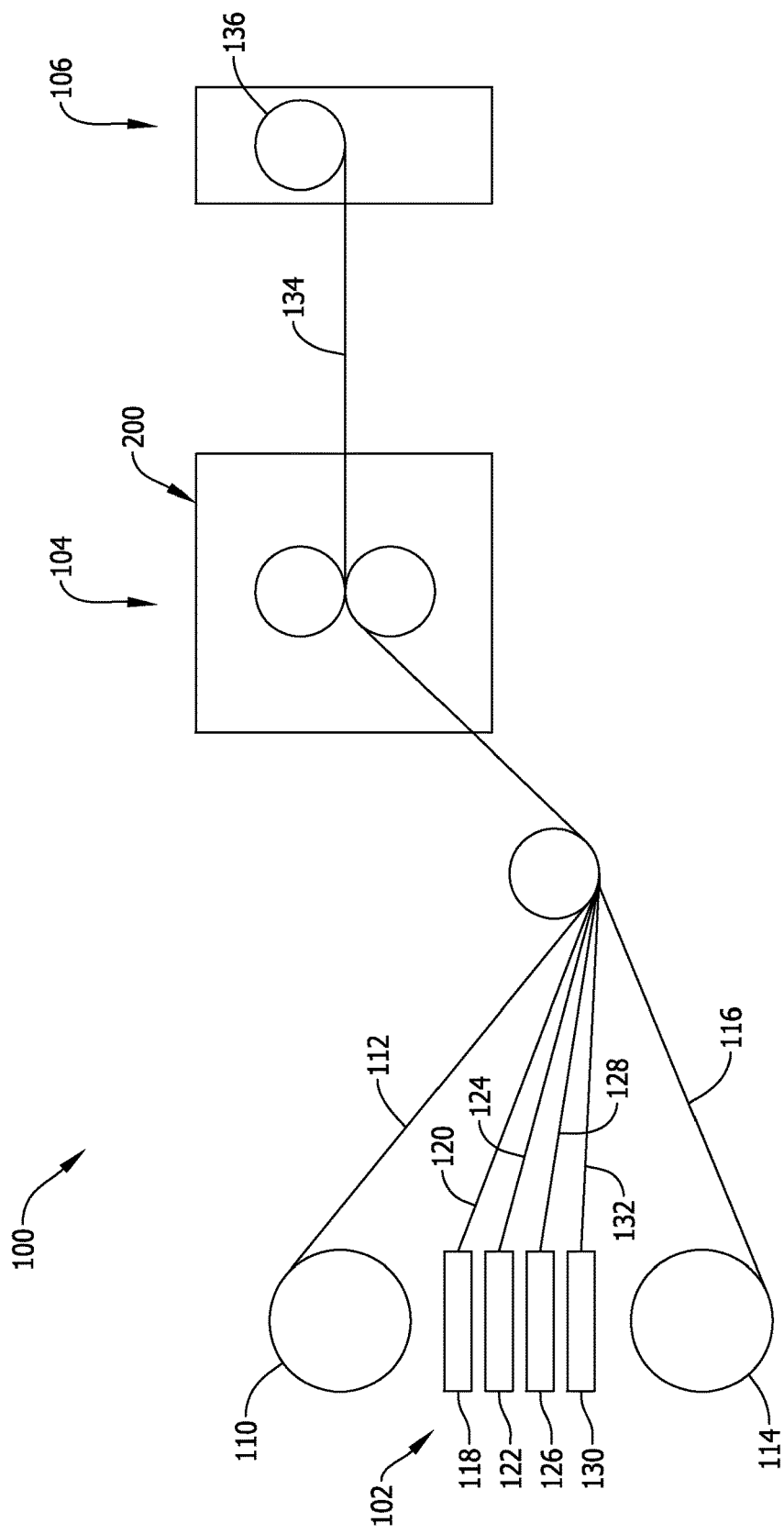
FIG. 1 is a schematic illustration of a system for fabricating an elastic nonwoven material.

Referring to the drawings, and in particular to FIG. 1, a system for fabricating an elastic nonwoven material is indicated generally by 100. The illustrated system 100 includes a supply station indicated generally by 102, a processing station indicated generally by 104, and a collection station indicated generally by 106. Other suitable stations are also contemplated without departing from the scope of this invention.

In the illustrated embodiment, the supply station 102 includes a plurality of supply rolls each containing a nonwoven fabric, namely a first supply roll 110 containing a first nonwoven fabric 112 and a second supply roll 114 containing a second nonwoven fabric 116. The supply station 102 also includes a plurality of supply spools each containing an elastic strand, namely a first supply spool 118 containing a first elastic strand 120, a second supply spool 122 containing a second elastic strand 124, a third supply spool 126 containing a third elastic strand 128, and a fourth supply spool 130 containing a fourth elastic strand 132. The elastic strands 120, 124, 128, 132 may have any suitable cross-sectional shape that facilitates enabling the elastic strands 120, 124, 128, 132 to function as described herein (e.g., a cross-sectional shape that is round, rectangular (e.g., relatively flat), square, etc.).

The illustrated processing station 104 includes a rotary ultrasonic bonding apparatus (indicated generally by 200) for bonding the elastic strands 120, 124, 128, 132 between the nonwoven fabrics 112, 116 to make an elastic nonwoven material 134, as set forth in more detail below. The collection station 106 may include any suitable device(s) for collecting the elastic nonwoven material 134 (e.g., a puller roll 136). In other embodiments, the supply station 102 may have any suitable quantity of supply rolls and supply spools having any suitable configuration that facilitates enabling the apparatus 200 to function as described herein.

FIGS. 2-7 are various embodiments of the rotary ultrasonic bonding apparatus 200. In the illustrated embodiments, the apparatus 200 has an anvil module 202 and a horn module 204 that cooperate to perform a bonding operation of the elastic strands 120, 124, 128, 132 between the nonwoven fabrics 112, 116 as set forth in more detail below.

In the illustrated embodiments, the horn module 204 includes a frame 206 on which are mounted a disc-like rotary horn 208, a motor 210 for driving rotation of the horn 208 via a suitable drive train 212, and a housing 214 which contains at least part of a vibration control unit (not shown) that causes the horn 208 to vibrate. The horn 208 has a face 216 with a substantially continuous contour (i.e., the horn face 216 has a contour that is substantially smooth (or uninterrupted) across its entire surface area). In other embodiments, the horn face 216 may have any suitable contour that facilitates enabling the horn 208 to function as described herein.

In some embodiments, the vibration control unit (while not illustrated) includes at least one booster (e.g., a drive booster and an integral booster) mechanically connected to a converter, which is electrically connectable to a generator. The converter is capable of converting high frequency electrical energy supplied by the generator into mechanical energy (or vibration) that is selectively transmitted to the horn 208 across the booster(s). The booster(s) are capable of modifying (i.e., increasing or decreasing) the vibration transmitted to the horn 208 from the converter, such that the horn 208 (particularly, the face 216 of the horn 208) vibrates while it rotates during a bonding operation, as set forth in more detail below. It is contemplated that the horn module 204 may have any suitable operational components arranged in any suitable manner that facilitates enabling the horn 208 to function as described herein.

In the illustrated embodiments, the anvil module 202 includes a frame 218 on which are mounted a disc-like rotary anvil 220 and a motor 222 for driving rotation of the anvil 220 via a suitable drive train 224. The anvil 220 has an annular face 226, the contour of which is not continuous (i.e., is interrupted) as set forth in more detail below. The anvil module 202 is positioned relative to the horn module 204 such that the anvil face 226 is rotatable in close proximity to the horn face 216, and vice versa, to facilitate ultrasonically bonding the elastic strands 120, 124, 128, 132 between the nonwoven fabrics 112, 116 when the elastic strands 120, 124, 128, 132 are held in tension across apparatus 200, as set forth in more detail below. As used herein, the term "close proximity" refers to when the anvil face 226 is either in contact with, or is minimally spaced apart from, the horn face 216 when the horn 208 is not ultrasonically vibrating.

In some embodiments, the apparatus 200 may be configured such that at least one of the anvil module 202 and the horn module 204 is displaceable relative to the other via a suitable displacement mechanism operable either: (A) when the system 100 is offline and the horn 208 is at rest (i.e., when the horn 208 is not rotating or vibrating); or (B) when the system 100 is online and the horn 208 is active (i.e., when the horn 208 is rotating and vibrating).

Figure 2:
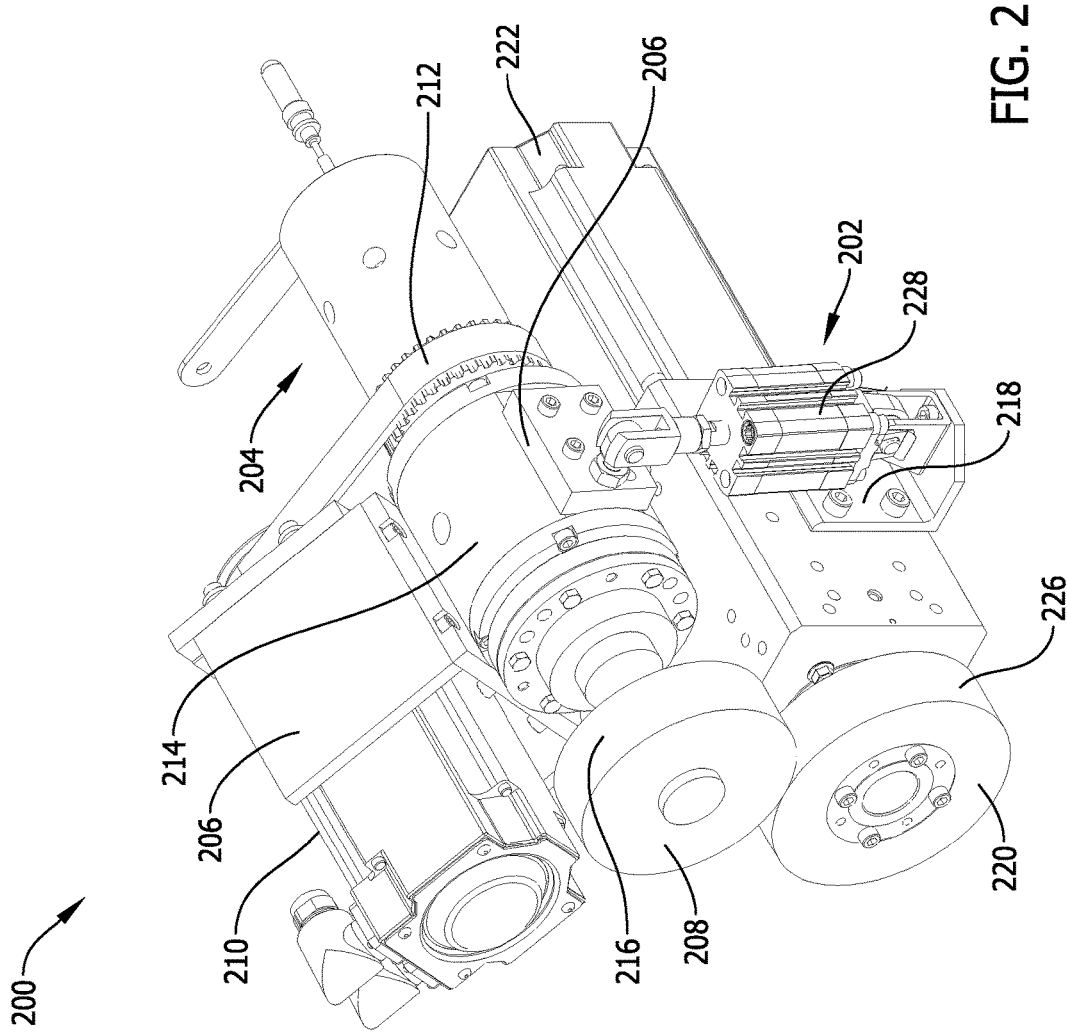
FIG. 2 is a perspective view of one embodiment of a rotary ultrasonic bonding apparatus for use in the system of FIG. 1.

With particular reference to the embodiment of FIG. 2, the apparatus 200 may be configured as a continuous-nip apparatus in which the horn module 204 is to be: (A) fixed in position relative to the anvil module 202 when the system 100 is online and the horn 208 is active; and (B) displaceable relative to the anvil module 202 when the system 100 is offline and the horn 208 is at rest. Such displacement is facilitated by a selectively actuatable pneumatic cylinder 228 (or other suitable linear actuator) that connects the frames 206, 218 to one another. In this manner, the spacing between the horn face 216 and the anvil face 226 is adjustable primarily for servicing the apparatus 200 when the system 100 is offline.

Figure 3:
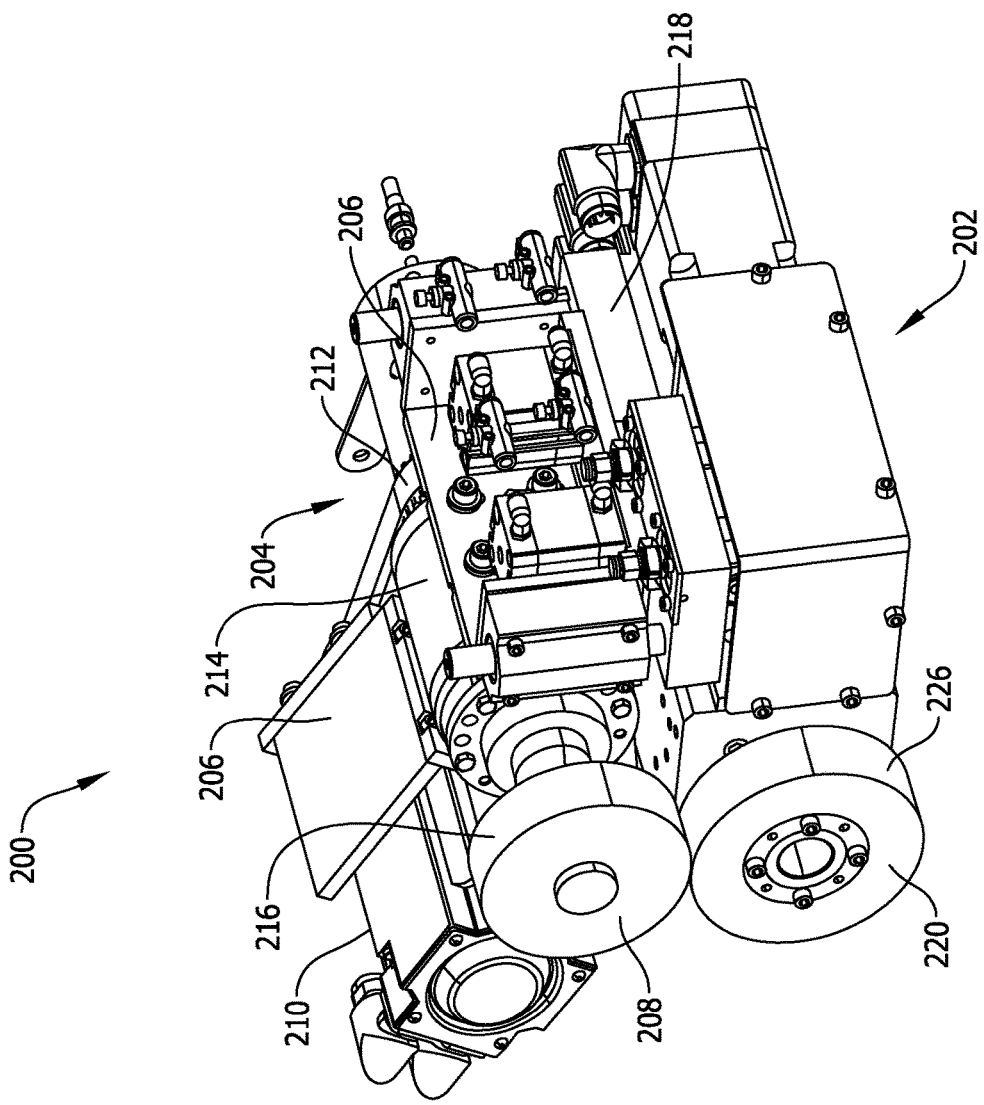
FIG. 3 is a perspective view of another embodiment of a rotary ultrasonic bonding apparatus for use in the system of FIG. 1.
Figure 4:
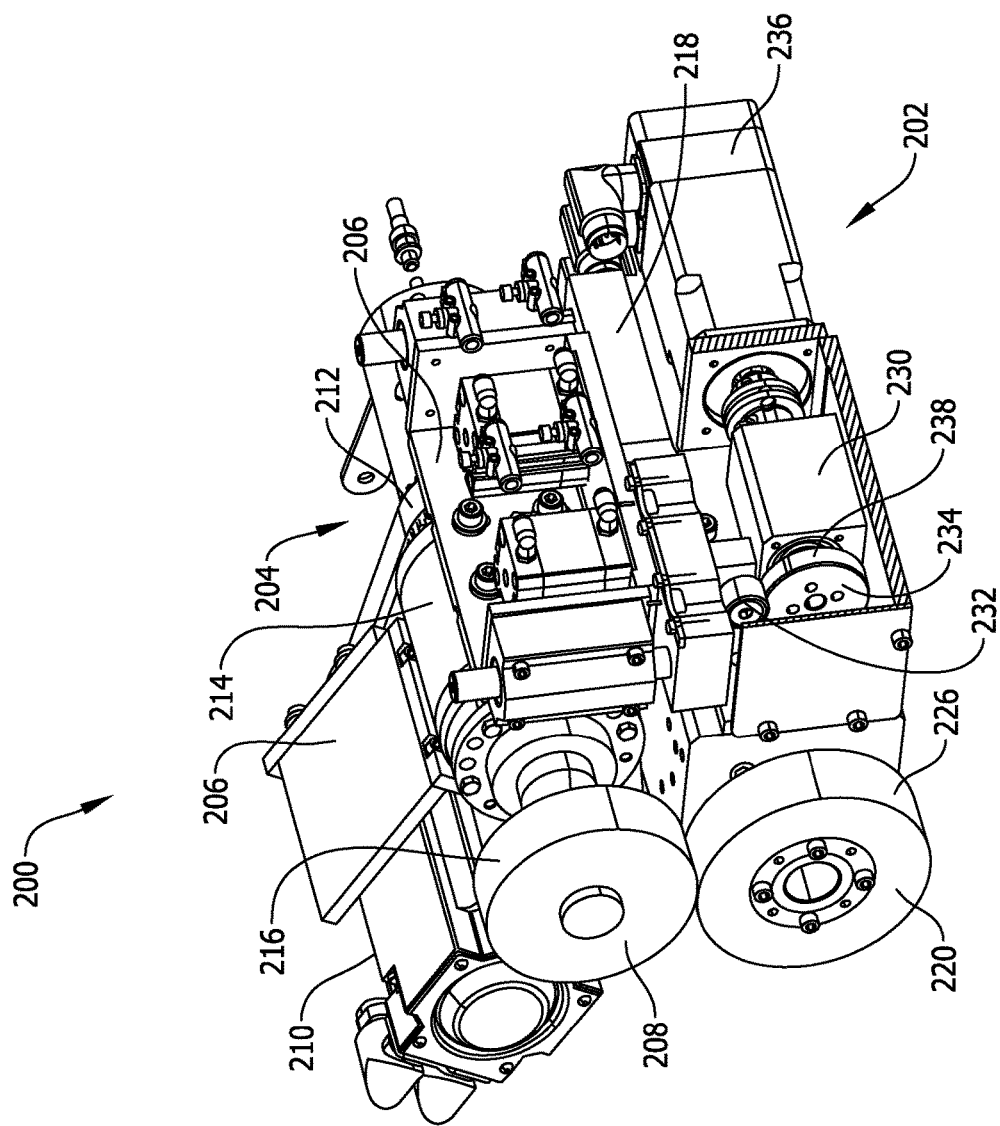
FIG. 4 is a partial cross-section of the apparatus of FIG. 3.

Referring now to the embodiment of FIGS. 3 and 4, the apparatus 200 may also be configured as an intermittent-nip apparatus in which the horn module 204 is displaceable relative to the anvil module 202 via a rotary camming device 230 when the system 100 is online and the horn 208 is active. The rotary camming device 230 has a follower 232 mounted to the horn module frame 206, and a cam wheel 234 mounted to the anvil module frame 218 and rotatable via a servomotor 236. The cam wheel 234 has an irregular camming surface 238 such that, when the cam wheel 234 is rotated via the servomotor 236, the follower 232 rides along the irregular camming surface 238 to cyclically displace the horn module frame 206 relative to the anvil module frame 218 at a predetermined frequency. In this manner, the spacing between the horn face 216 and the anvil face 226, and/or the frequency at which the horn face 216 contacts the anvil face 226, are selectively adjustable. Other displaceable arrangements of the horn module 204 and the anvil module 202 are also contemplated without departing from the scope of this invention.

Figure 5:
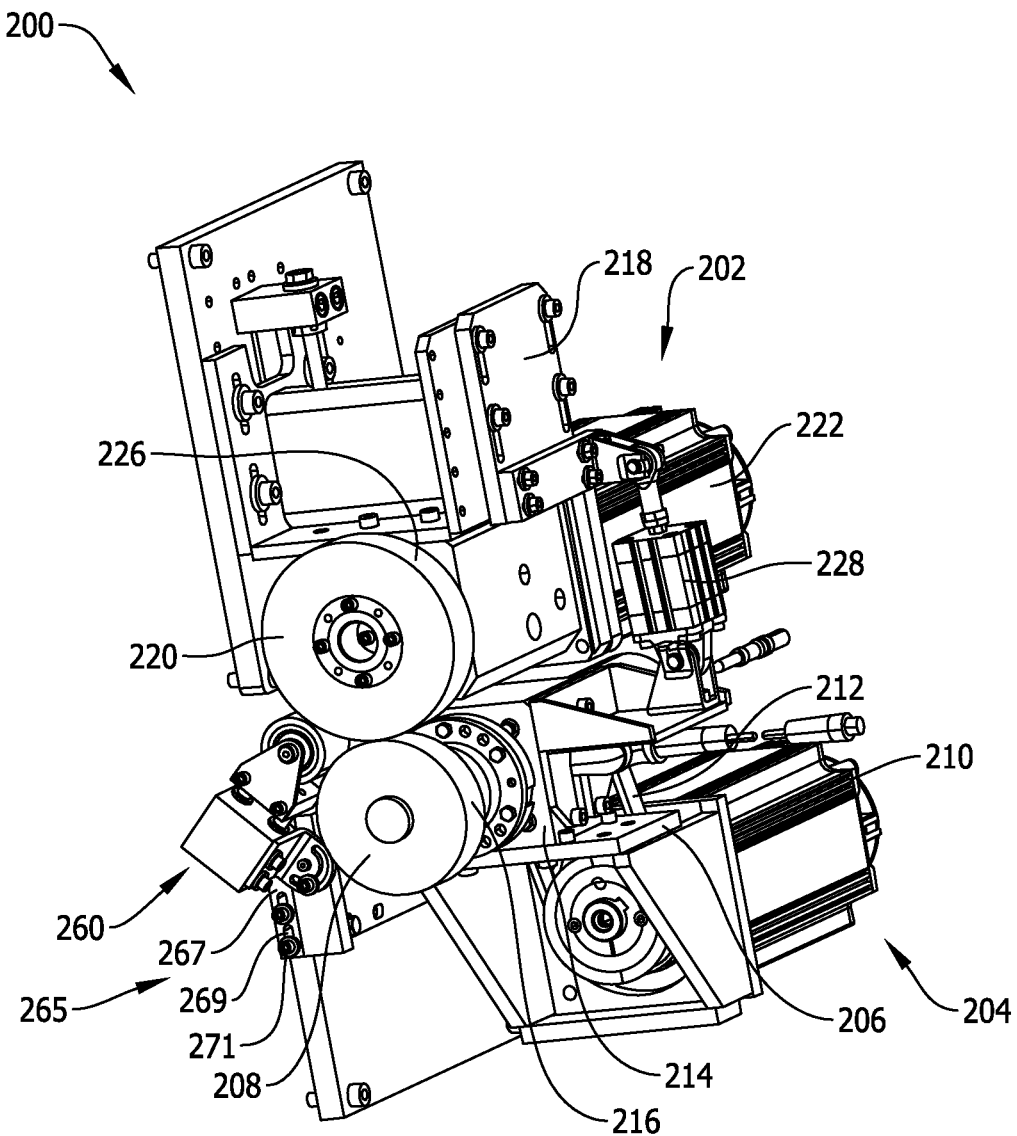
FIG. 5 is a perspective view of another embodiment of a rotary ultrasonic bonding apparatus for use in the system of FIG. 1.
Figure 6:
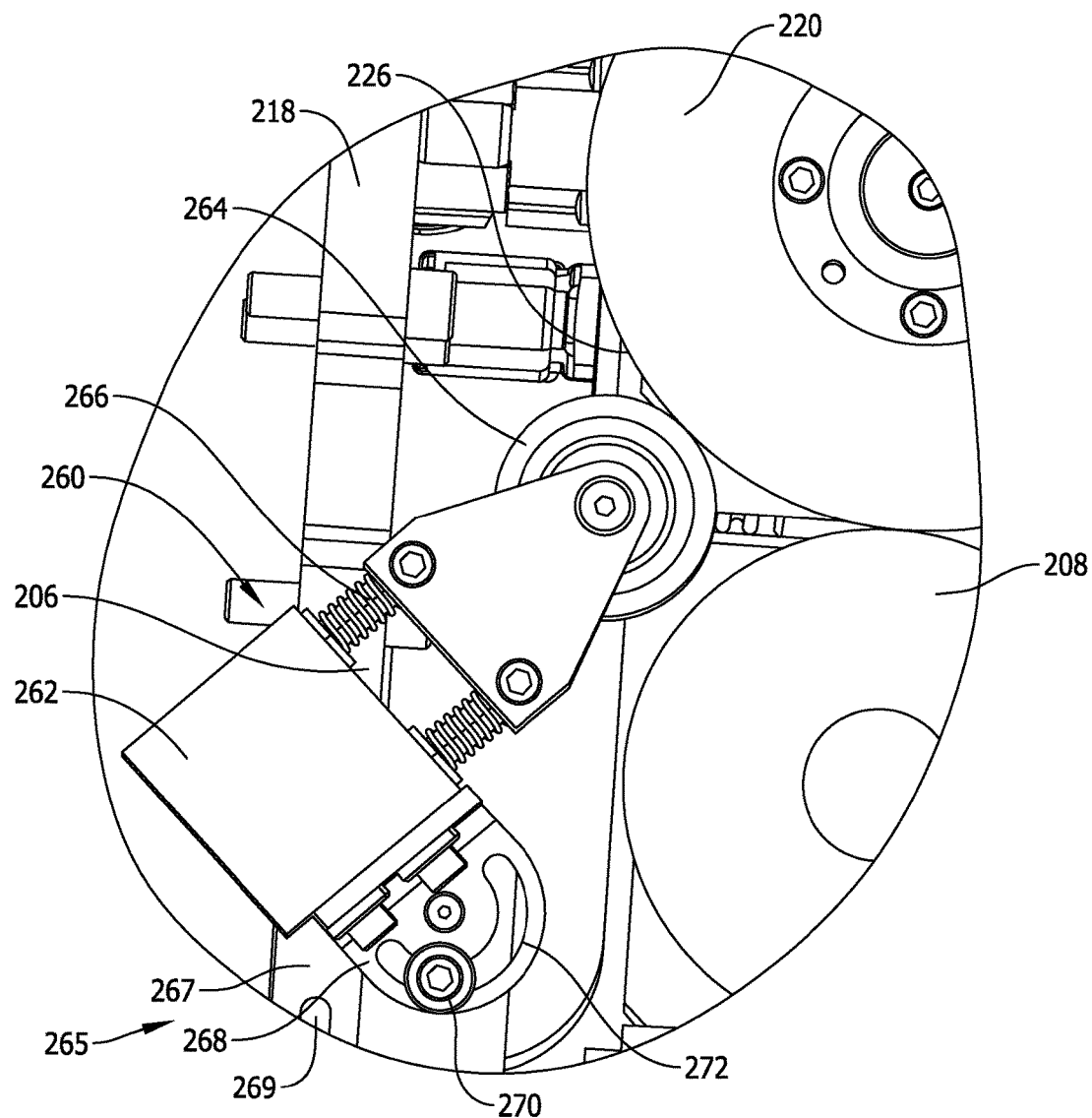
FIG. 6 is an enlarged side elevation view of a pinching device of the apparatus of FIG. 5.

As shown in the embodiment of FIGS. 5 and 6, the apparatus 200 may also include a pinching device 260. In the illustrated embodiment, the pinching device 260 includes a base 262 and a roller 264 floatingly mounted to the base 262 via at least one biasing element 266. The pinching device 260 also includes a bracket assembly 265 by which the base 262 and the roller 264 are mounted to at least one of the frame 206 and the frame 218, such that the base 262 and the roller 264 are adjustable in at least two degrees of freedom (as set forth in more detail below) in relation to the anvil 220 to facilitate use of the pinching device 260 in conjunction with anvils of different sizes.

The illustrated bracket assembly 265 includes a first bracket 267 and a second bracket 268. The first bracket 267 has at least one linear slot 269 through which a bolt 271 (which is fixed to either the frame 206 of the horn module 204 or the frame 218 of the anvil module 202) extends, and along which the bolt 271 is slidable, thereby rendering the first bracket 267 translatable relative to the frame 206 and/or 218. The second bracket 268 has at least one substantially arcuate slot 272 through which a bolt 270 (which is fixed to the first bracket 267) extends, and along which the bolt 270 is slidable, thereby rendering the second bracket 268 rotatable relative to the first bracket 267. The base 262 is mounted to the second bracket 268 such that the base 262 (and, therefore, the roller 264) are rotatably adjustable in a first degree of freedom via rotation of the second bracket 268, and are translatably adjustable in a second degree of freedom via translation of the first bracket 267.

The position of the base 262 and, therefore, the roller 264 are fixable via the bolt 270 and the bolt 271 to achieve a desired pinching contact between the roller 264 and the anvil face 226. For example, in the illustrated embodiment, the base 262 and the roller 264 are oriented such that the biasing element 266 applies a biasing force oriented substantially perpendicular to a rotation axis of the anvil 220 when viewed as in FIG. 6. In other embodiments, the pinching device 260 may have any suitable components arranged and movable (e.g., translatable and/or rotatable) in any suitable manner that facilitates enabling the pinching device 260 to perform the pinching action described herein (e.g., on any suitable bracket assembly that facilitates enabling the base 262 and the roller 264 to be adjustable in at least two degrees of freedom such as, for example, two translating degrees of freedom, or one translating degree of freedom and one rotating degree of freedom).

In this manner, the pinching device 260 limits the snap-back potential of elastic strands 120, 124, 128, 132 that become severed between horn 208 and anvil 220 during a bonding operation. More specifically, the pinching device 260 effectively catches broken elastic strand(s) 120, 124, 128, 132 between the roller 264 and the anvil 220 to prevent the broken elastic strands 120, 124, 128, 132 from snapping back to their respective supply spool(s) 118, 122, 126, 130. Moreover, because the roller 264 rotates by virtue of being in contact with anvil 220, any broken elastic strands 120, 124, 128, 132 are caught at the interface of roller 264 and anvil 220 and are automatically fed back into the interface between horn 208 and anvil 220. As such, the pinching device 260 serves as a self-threading device for broken elastic strands 120, 124, 128, 132.

Figure 7:
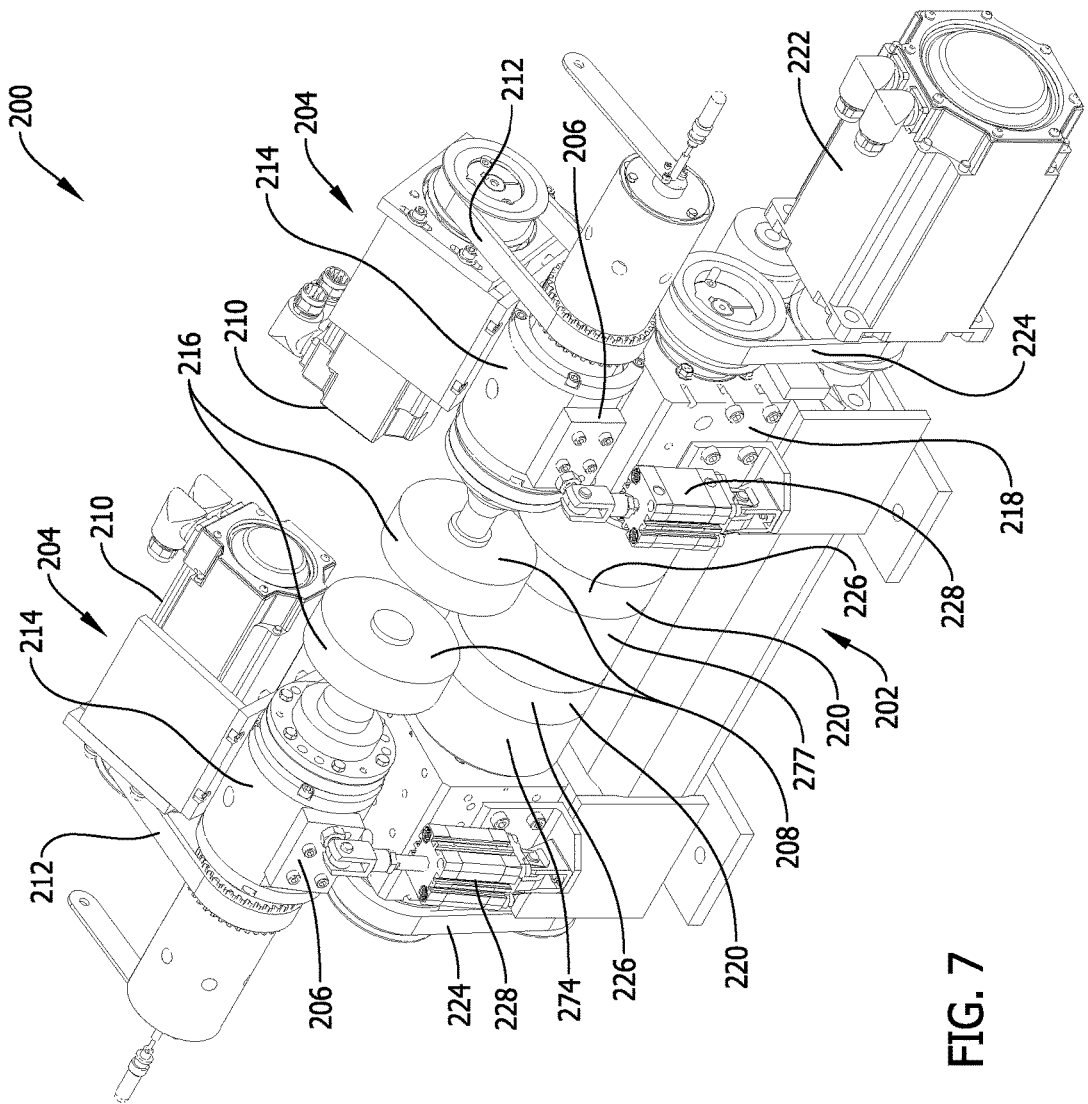
FIG. 7 is a perspective view of yet another embodiment of a rotary ultrasonic bonding apparatus for use in the system of FIG. 1.

Notably, the apparatus 200 may have any suitable quantity of anvil modules 202 and/or horn modules 204 that cooperate with one another to facilitate enabling the apparatus 200 to function as described herein. For example, as illustrated in the embodiment of FIG. 7, the apparatus 200 may be configured with an anvil drum 274 in which a pair of anvils 220 are positioned such that the drum 274 has a pair of predefined, annular faces 226 that are spaced apart from one another. In this manner, the horn 208 of a separate horn module 204 is dedicated to each such anvil face 226, thereby facilitating a bonding operation on confined regions of larger nonwoven fabrics on which only partial elasticity is desired (e.g., segments of these larger nonwoven fabrics on which elasticity is not desired may move along non-contact regions 277 of the drum 274 to avoid interaction with the associated horn(s) 208).

To facilitate minimizing the occurrence of elastic strands 120, 124, 128, 132 being cut between the horn 208 and the anvil 220 during a bonding operation, it is desirable to effectively hold the elastic strands 120, 124, 128, 132 in place within notches of the anvil face 226 while the nonwoven fabrics 112, 116 are bonded together between the horn 208 and the anvil 220. At least the following operational parameters contribute to minimizing the occurrence of elastic strands 120, 124, 128, 132 being cut during a bonding operation: (A) the specific energy source (e.g., the amplitude of vibration of the horn 208 and its pressure when contacting the anvil 220); (B) the energy director (e.g., the geometry of the anvil face 226); and (C) the material system (e.g., the decitex and tension of the elastic strands 120, 124, 128, 132, and the basis weight of the nonwoven fabrics 112, 116).

Figure 8:
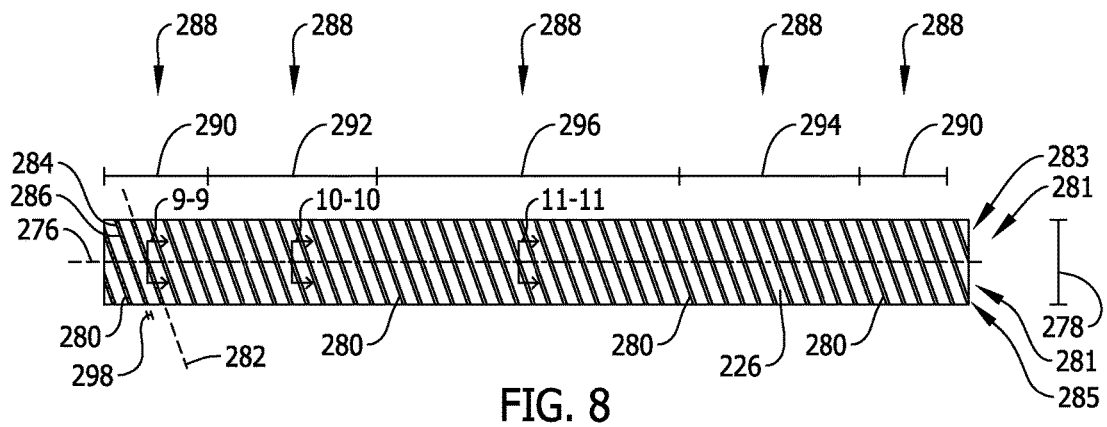
FIG. 8 is a laid-flat illustration of an annular face of one embodiment of an anvil for use in the apparatuses of FIGS. 2-7.

With respect to one such parameter (i.e., the geometry of the anvil face 226), FIG. 8 is a laid-flat illustration of an embodiment of the anvil face 226 of the apparatus 200. In the illustrated embodiment, the anvil face 226 has a circumferential centerline axis 276 and a width dimension 278 oriented perpendicular to the axis 276. The contour of the anvil face 226 is irregular (i.e., not continuous) along the axis 276, in that the anvil face 226 defines a plurality of circumferentially spaced ridges 280. For example, in some embodiments, each adjacent pair of ridges 280 may have a spacing (or pitch) measured along the axis 276 of between about 0.10 inches and about 1.00 inches (e.g., between about 0.20 inches and about 0.50 inches). While all adjacent pairs of ridges 280 on the anvil face 226 are substantially equally spaced apart from one another in the illustrated embodiment, it is contemplated that the spacing between adjacent pairs of ridges 280 may vary along the axis 276 in other embodiments.

Figure 9:
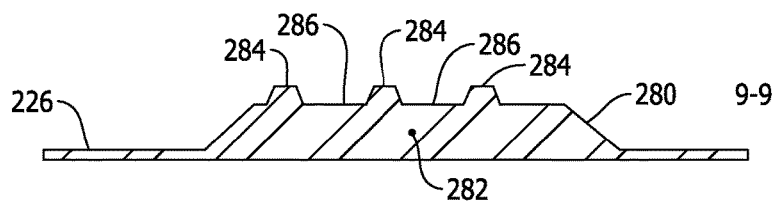
FIG. 9 is a cross-section, taken along plane 9-9 of FIG. 8, of one embodiment of a ridge defined by the anvil face of FIG. 8.

In the illustrated embodiment, each ridge 280 extends substantially linearly across the circumferential axis 276 so as to span substantially the entire width 278 of the anvil face 226. Each ridge 280 has an extension axis 282 oriented oblique to the circumferential axis 276. As illustrated in FIG. 9, each ridge 280 includes a plurality of lands 284 spaced along its extension axis 282 such that each adjacent pair of lands 284 is spaced apart by (or flank) a notch 286. While the lands 284 and notches 286 are illustrated on only a select few of the ridges 280 in FIG. 8, it is understood that all ridges 280 of anvil face 226 likewise have a set of lands 284 and notches 286 along their respective extension axes 282. Notably, adjacent ones of the lands 284 of each ridge 280 are shaped such that the corresponding notch 286 defined therebetween is oriented substantially parallel to the circumferential axis 276 (i.e., the ridges 284 and the notches 286 each have a lengthwise dimension 298 that is oriented substantially parallel to the circumferential axis 276 in the illustrated embodiment).

In some embodiments, the anvil face 226 may be configured for a continuous entrapment bonding operation. More specifically, in such embodiments, each of the ridges 280 has at least one notch 286 that is aligned in the width dimension 278 with a corresponding notch 286 of each other ridge 280, and the lands 284 that flank each aligned notch 286 are spaced to create widthwise adjacent bonds in the nonwoven fabrics 112, 116 that are close enough together in the width dimension 278 to permanently hold the associated elastic strand 120, 124, 128, 132 in tension therebetween. As a result, after the bonding operation is complete and the nonwoven fabrics 112, 116 are removed from the system 100, at least one of the elastic strands 120, 124, 128, 132 is subsequently permitted to contract between circumferentially adjacent rows of bonds, but not between the widthwise adjacent bonds through which the elastic strand(s) 120, 124, 128, 132 extend. The entrapment bonding operation is therefore said to be continuous in the sense that at least one of the elastic strands 120, 124, 128, 132 is caused to be permanently held in tension between each widthwise adjacent pair of bonds through which it extends.

In one embodiment of a continuous entrapment configuration of the anvil face 226, the lands 284 and the notches 286 of each ridge 280 have sizes (and, therefore, spacings) relative to one another that are substantially the same as those of all other ridges 280 on the anvil face 226. The notches 286 are generally U-shaped or generally V-shaped, such that the sidewalls of the lands 284 that flank each notch 286 may, when viewed from a cross-sectional profile of the notch 286 as shown in FIG. 9, form a wedge angle therebetween of about 0° (i.e., the sidewalls may be about parallel to one another) and about 140° (e.g., between about 60° and about 100°). Notches 286 of other shapes are also contemplated.

In one particular embodiment, if the elastic strands 120, 124, 128, 132 have a decitex of between about 540.0 and about 1240.0, and if the nonwoven fabrics 112, 116 have a grammage (gsm) of between about 11.0 and 16.0, the lands 284 may have lengths at their peaks of between about 0.010 inches and about 0.25 inches (e.g., between about 0.030 inches and about 0.060 inches), and widths at their peaks of between about 0.008 inches and about 0.050 inches (e.g., between about 0.010 inches and about 0.030 inches). Also, in that example, the notches 286 may have: depths measured from the peaks of their flanking lands 284 of between about 0.005 inches and about 0.020 inches (e.g., between about 0.007 inches and about 0.010 inches); widths measured at the peaks of their flanking lands 284 of between about 0.006 inches and about 0.016 inches (e.g., between about 0.008 inches and about 0.012 inches); and widths measured at their bases of between about 0.0025 inches and about 0.010 inches (e.g., between about 0.003 inches and about 0.005 inches).

By providing the lands 284 and the notches 286 with the dimensions of the above example, the anvil face 226 facilitates improved gripping of the elastic strands 120, 124, 128, 132 in the notches 286 and, therefore, facilitates preventing the elastic strands 120, 124, 128, 132 from withdrawing out of the notches 286 to reduce the occurrence of severed elastic strands 120, 124, 128, 132. Other suitable sizes for the lands 284 and the notches 286 are also contemplated without departing from the scope of this invention.

In other embodiments, the anvil face 226 may be configured for an intermittent entrapment bonding operation, such that the lands 284 that flank at least one of the notches 286 are spaced to create widthwise adjacent bonds in the nonwoven fabrics 112, 116 that are not close enough together in the width dimension 278 to permanently hold the associated elastic strand 120, 124, 128, 132 in tension therebetween. As a result, after the bonding operation is complete and the nonwoven fabrics 112, 116 are removed from the system 100, the corresponding elastic strand 120, 124, 128, 132 is subsequently permitted to contract between the widthwise adjacent bonds through which it extends such that its tension between those widthwise adjacent bonds is substantially relieved. The entrapment bonding operation is therefore said to be intermittent in the sense that at least one of the elastic strands 120, 124, 128, 132 is not permanently held in tension between all pairs of widthwise adjacent bonds through which it extends.

In one embodiment of an intermittent entrapment configuration of the anvil face 226, the anvil face 226 may be provided with a plurality of distinct circumferential regions 288 such that a dimension of a notch 286 (and, therefore, the lands 284 that flank it) on a ridge 280 in at least one circumferential region 288 is different than a dimension of a widthwise aligned notch 286 (and, therefore, the lands 284 that flank it) on a ridge 280 in at least one other circumferential region 288.

Figure 10:
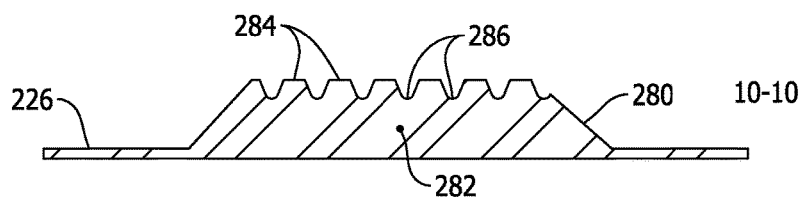
FIG. 10 is a cross-section, taken along plane 10-10 of FIG. 8, of another embodiment of a ridge defined by the anvil face of FIG. 8.

For example, each ridge 280 in a plurality of first circumferential regions 290, 296 may have at least one notch 286 that is sized differently as compared to at least one notch 286 that is widthwise aligned therewith on ridges 280 in a plurality of second circumferential regions 292, 294 interspaced between the first circumferential regions 290, 296. In this example, within the first circumferential regions 290, 296, the notches 286 may be sized with larger widths (like in FIG. 9) such that the elastic strands 120, 124, 128, 132 do not later become entrapped across (i.e., are later permitted to slip between) the widthwise adjacent bonds created at widthwise adjacent lands 284 on ridges 280 in these first circumferential regions 290, 296. Whereas, within the second circumferential regions 292, 294, the notches 286 may be sized with smaller widths (like in FIG. 10) such that the elastic strands 120, 124, 128, 132 later become entrapped across (i.e., are not later permitted to slip between) the widthwise adjacent bonds created at widthwise adjacent lands 284 on ridges 280 in the second circumferential regions 292, 294.

More specifically, in this example, at least one ridge 280 in each second circumferential region 292, 294 may have its notches 286 sized in the manner set forth above for the continuous entrapment example, while at least one ridge 280 in each first circumferential region 290, 296 may have its notches 286 sized with a width (as measured at the peaks of its flanking lands 284) of between about 0.010 inches and about 0.25 inches (e.g., between about 0.030 inches and about 0.060 inches in some embodiments; or about 0.035 inches in one particular embodiment). Thus, adequate slippage of the elastic strands 120, 124, 128, 132 across at least one ridge 280 in each first circumferential region 290, 296 is facilitated, especially when the elastic strands 120, 124, 128, 132 have a decitex of between about 540.0 and about 1240.0, and when the nonwoven fabrics 112, 116 have a grammage (gsm) of between about 11.0 and 16.0.

Figure 11:
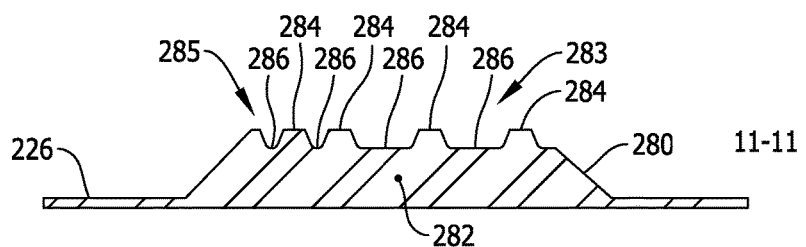
FIG. 11 is a cross-section, taken along plane 11-11 of FIG. 8, of yet another embodiment of a ridge defined by the anvil face of FIG. 8.

In both a continuous entrapment configuration and an intermittent entrapment configuration, the anvil face 226 may have a plurality of distinct widthwise segments 281, wherein each widthwise segment 281 has lands 284 and/or notches 286 of comparatively different sizes. For example, in one particular embodiment illustrated by FIG. 11, the anvil face 226 may have a first widthwise segment 283 with lands 284 that define notches 286 of a first width to suit elastic strands 120, 124, 128, 132 of a first decitex, and a second widthwise segment 285 with lands 284 that define notches 286 of a second width that is less than the first width to suit elastic strands 120, 124, 128, 132 of a second decitex that is less than the first decitex. Thus, each widthwise segment 281, no matter whether it is configured for continuous or intermittent entrapment, may be sized to accommodate elastic strands 120, 124, 128, 132 of different sizes.

Figure 12:
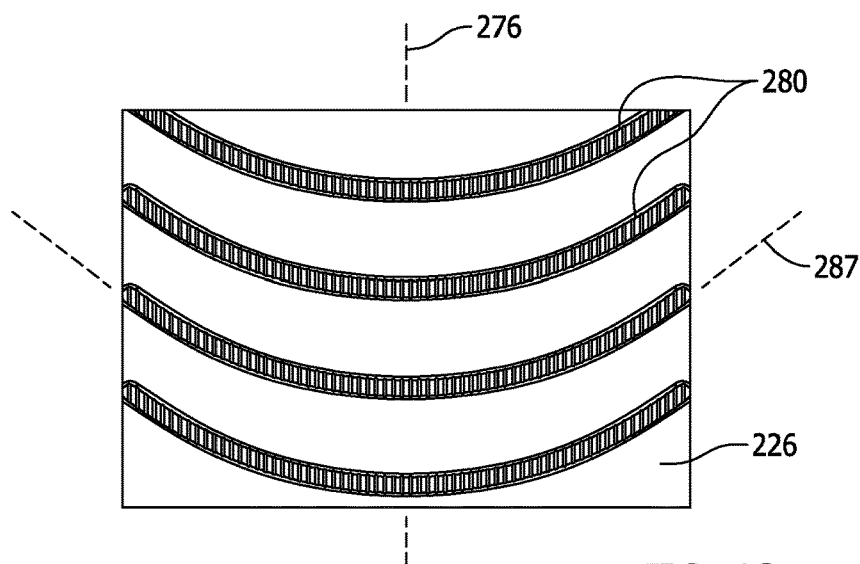
FIG. 12 is a laid-flat illustration of a portion of an annular face of another embodiment of an anvil for use in the apparatuses of FIGS. 2-7.
Figure 13:
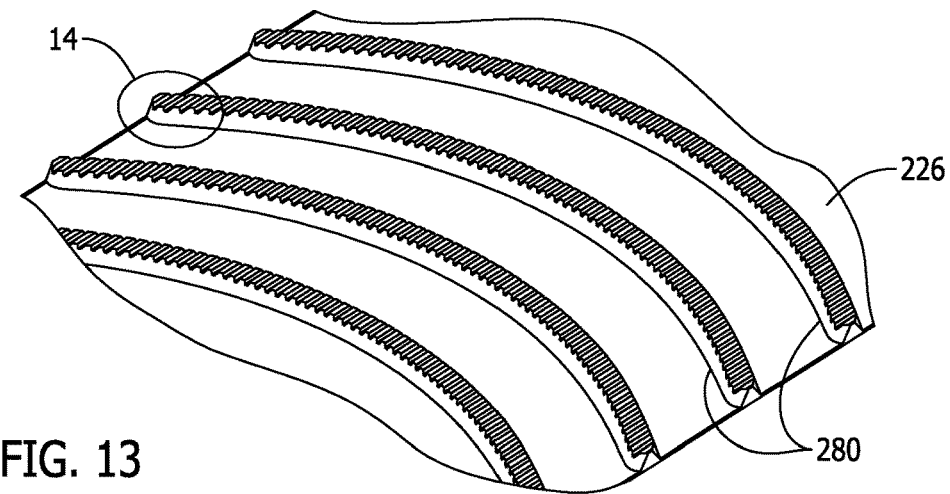
FIG. 13 is a perspective view of the portion of the annular face of FIG. 12.
Figure 14:
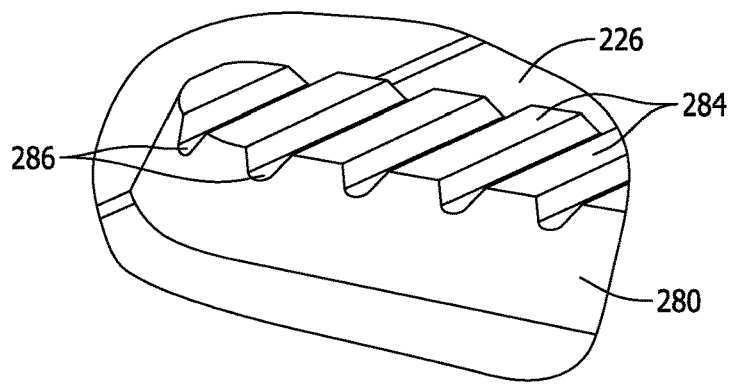
FIG. 14 is an enlarged segment of the perspective view of FIG. 13 taken within area 14 of FIG. 13.

In yet other embodiments, the anvil face 226 may have ridges 280 that extend non-linearly across the circumferential axis 276. For example, in one particular embodiment illustrated by FIGS. 12-14, the anvil face 226 may define a plurality of ridges 280 each with a curvilinear axis (e.g., a substantially arcuate axis 287). Notably, these embodiments with non-linear ridges 280 may have the same dimensions for the lands 284 and the notches 286 as for the substantially linearly extending ridges 280 set forth above, including the same dimensional variations amongst circumferential and widthwise regions 288, 281 as is set forth above with respect to the substantially linearly extending ridges 280.

Figure 15:
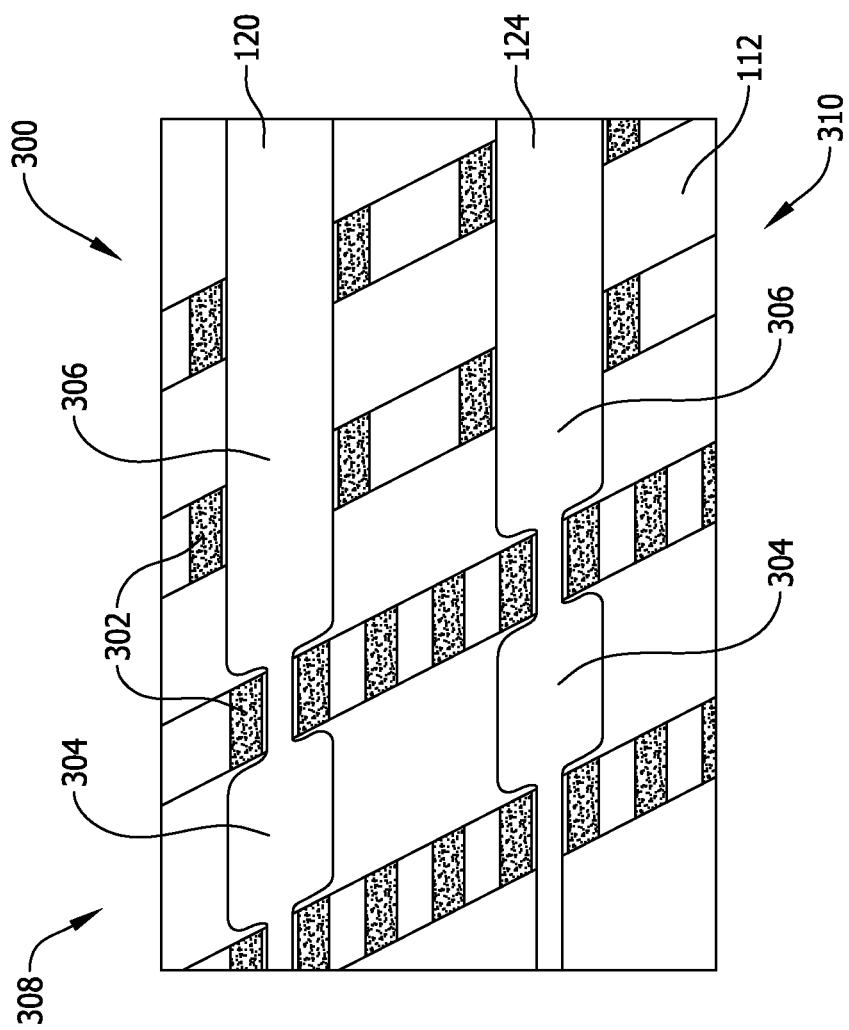
FIG. 15 is a schematic illustration of an elastic nonwoven material fabricated using an embodiment of the system of FIG. 1.

FIG. 15 illustrates an elastic nonwoven material 300 fabricated using the system 100. In the illustrated embodiment, an intermittent entrapment bonding process was performed on the nonwoven fabrics 112, 116 (with elastic strands 120, 124 sandwiched therebetween) using one of the embodiments of the apparatus 200 set forth above. The embodiment of the anvil 220 utilized to fabricate the material 300 has an anvil face 226 with notches 286 that vary in size across circumferential regions 288 as set forth in some of the embodiments above. In this manner, with the nonwoven fabrics 112, 116 and the elastic strands 120, 124 held in tension across the apparatus 200, the horn face 216 and the anvil face 226 created bonds 302 at locations corresponding to the lands 284 of the anvil face 226.

Once the bonded nonwoven fabrics 112, 116 (and the elastic strands 120, 124 sandwiched therebetween) were subsequently removed from the system 100, the tension in the elastic strands 120, 124 was partly relieved such that segments of each elastic strand 120, 124 were permitted to contract to create material 300. More specifically, a first segment 304 of each elastic strand 120, 124 became entrapped between adjacent rows of bonds 302 that corresponded to the ridges 280 which defined notches 286 of smaller widths. Whereas, a second segment 306 of each elastic strand 120, 124 was permitted to slip across widthwise adjacent bonds 302 in rows that corresponded to the ridges 280 which defined notches 286 of larger widths. In this manner, the nonwoven fabrics 112, 116 were caused to gather in areas 308 of the material 300 that have widthwise adjacent bonds 302 of closer spacing (but not in areas 310 that have widthwise adjacent bonds 302 of greater spacing) to effectively provide the material 300 with an elastic property. Notably, if a continuous entrapment operation had been utilized instead of an intermittent entrapment operation, the material 300 would not have second segments 306 that are permitted to slip, but would instead only have first segments 304 such that the nonwoven fabrics 112, 116 would gather along the entire material 300.

The rotary ultrasonic bonding systems and methods set forth herein are utilized to directly entrap tensioned elastic within a nonwoven fabric without the use of adhesives, thereby providing various functional and commercial advantages. The systems and methods eliminate the complex adhesive delivery systems and costly adhesive materials associated with adhesive bonding processes, and the systems and methods provide a simpler, cleaner, and safer (e.g., cooler in temperature) production environment, with lower power consumption and lower material costs. Also, various functional deficiencies of adhesively bonded materials are eliminated, including adhesive bleed-through, stiffening, and creep that are common in conventional adhesively bonded materials. Thus, lower-cost nonwoven/film substrates and elastic materials can be utilized.

Moreover, the systems and methods set forth herein facilitate a more continuous production sequence (i.e., increased process uptime) due, at least in part, to the lack of: adhesive-related cleaning operations; adhesive system delivery/reliability issues; heated equipment cool-down periods in advance of maintenance events; cold-start periods; and re-heat or purge-calibrate events. Additionally, a more continuous production sequence is further facilitated by the automatic threading (or self-threading) of severed elastic strands when the system is online, as well as the use of continuously-running, over-the-end elastic spools.

Additionally, the systems and methods set forth herein are usable to attach (e.g., entrapment) elastic strands while also performing other elastic processing steps such as cutting/chopping processes, seaming processes, edge trimming processes, etc. The systems and methods are further adaptable to existing capital asset bases to provide retrofit capability (with customizable configurations if desired), as well as quicker grade-change capability as the attachment zone length changes via a software interface.

The systems and methods also facilitate maximizing elastic performance. For example, the systems and methods facilitate lowering tension at elongation as compared to other attachment methods (e.g., the systems and methods can provide a nearly pure elastic response for stress vs. strain when at least some substrates are utilized). The systems and methods also facilitate minimizing creep (or loss of performance) (e.g., the systems and methods produce elastic materials that are more robust in the face of temperature, time, and end-user solvents (e.g., emollients)) due, at least in part, to the fact that the elastic strands can be entrapped in a thermoplastic substrate, as opposed to being attached to a substrate with a susceptible intermediate binder material.

The systems and methods further facilitate customized aesthetics and functional benefits. For example, gathers are produced by a bonding pattern and/or strand-feed positioning such that size, shape, and frequency are selectable. Also, zoned tension is enabled, in that tension can be controlled by an elastic segment depending upon the desired fabric configuration (e.g., depending upon the desired cross-direction orientation within fabric (among lanes) and/or longitudinal orientation within fabric (within lanes)). Curved attachment is also facilitated if desired. Furthermore, controlled slip/creep for adjustable fit is facilitated, with intermittent or continuous attachment of elastic to the substrate being selectable to enable placement/zoning of live elastic and non-elasticized segments.

In addition to the embodiments of the systems and methods set forth above, other embodiments are also contemplated. For example, non-rotary systems of attachment (e.g., stationary (or blade) ultrasonic horns, heat, pressure, etc.) are contemplated. Also, in combination with the rotary embodiments set forth above, adhesive systems may be usable in alternative embodiments. Moreover, latent elastics may be usable instead of tensioned elastics in some embodiments. Then too, the systems and methods facilitate curving (or shifting) elastic strands with less occurrence of breakage, and the systems and methods further facilitate generating a matrix of tensions (e.g., a checkerboard effect), differential ruffling, dead zones, and/or simultaneous incorporation of elastic strands of different decitex.

Notably, the systems and methods described herein facilitate fabricating a variety of elastic nonwoven materials usable in a variety of articles such as personal care articles (e.g., adult briefs, baby diapers, child/adult pull-on pants, contour fit hygiene products, etc.) or medical garments (e.g., masks, caps, gowns, footwear, etc.). Moreover, individual components (e.g., scrim/netting, diaper ears, discreet panels, etc.) of an article can be fabricated using elastic nonwoven materials fabricated via the above-described systems and methods. Other contemplated products in which the nonwoven materials can be utilized include thermal insulation or filters (e.g., associated ruffling or blousing), as well as elastic-topped garbage bags, non-adhesive bandages, hair nets, house wrap, etc.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An apparatus for fabricating an elastic nonwoven material, said apparatus comprising:
   a first bonding module; and
   a second bonding module positionable in close proximity to the first bonding module, wherein one of the first bonding module and the second bonding module has a face with a width and a circumferential axis, the face having a plurality of ridges each of which defines a plurality of interspaced lands and notches, the notches oriented substantially parallel to the circumferential axis.

2. The apparatus of claim 1, wherein the ridges extend obliquely across the circumferential axis.

3. The apparatus of claim 1, wherein the ridges extend across substantially the entire width of the face.

4. The apparatus of claim 1, wherein all pairs of adjacent ridges on the face are substantially equally spaced apart from one another along the circumferential axis.

5. The apparatus of claim 1, wherein an adjacent pair of ridges has a spacing measured along the circumferential axis of between about 0.10 inches and about 1.00 inches.

6. The apparatus of claim 5, wherein the spacing is between about 0.20 inches and about 0.50 inches.

7. The apparatus of claim 1, wherein all of the notches on the face are substantially the same size.

8. The apparatus of claim 1, wherein one of the notches is flanked by a pair of the lands, each of the flanking lands having a peak such that the one notch has a width measured at the peaks of the flanking lands of between about 0.006 inches and about 0.016 inches.

9. The apparatus of claim 8, wherein the width is between about 0.008 inches and about 0.012 inches.

10. The apparatus of claim 1, wherein one of the notches is flanked by a pair of the lands, each of the flanking lands having a peak such that the one notch has a depth measured from the peaks of the flanking lands of between about 0.005 inches and about 0.020 inches.

11. The apparatus of claim 10, wherein the depth is between about 0.007 inches and about 0.010 inches.

12. The apparatus of claim 1, wherein one of the notches is flanked by a pair of the lands, each of the flanking lands having a peak such that the one notch has a width measured at the peaks of the flanking lands of between about 0.010 inches and about 0.25 inches.

13. The apparatus of claim 12, wherein the width is between about 0.030 inches and about 0.060 inches.

14. The apparatus of claim 13, wherein the width is about 0.035 inches.

15. The apparatus of claim 1, wherein each of the lands has a peak, one of the lands having a length measured at its peak of between about 0.010 inches and about 0.25 inches.

16. The apparatus of claim 15, wherein the length is between about 0.030 inches and about 0.060 inches.

17. The apparatus of claim 1, wherein each of the lands has a peak, one of the lands having a width measured at its peak of between about 0.008 inches and about 0.050 inches.

18. The apparatus of claim 17, wherein the width is between about 0.010 inches and about 0.030 inches.

19. The apparatus of claim 1, wherein the other one of the first bonding module and the second bonding module has a face with a contour that is substantially continuous.

20. The apparatus of claim 1, wherein the face has a first circumferential region with ridges defining notches of a first size, and a second circumferential region with ridges defining notches of a second size different than the first size.

21. The apparatus of claim 20, wherein the face defines a spaced-apart pair of the first circumferential regions and a spaced-apart pair of the second circumferential regions.

22. The apparatus of claim 1, wherein the face has a first widthwise region in which the ridges define notches of a first size, and a second widthwise region in which the ridges defining notches of a second size different than the first size.

23. The apparatus of claim 1, wherein the ridges extend substantially linearly across the circumferential axis.

24. The apparatus of claim 1, wherein the ridges extend non-linearly across the circumferential axis.

25. The apparatus of claim 24, wherein the ridges extend substantially arcuately across the circumferential axis.

26. The apparatus of claim 1 further comprising
a camming device displaceably connecting the first and second bonding modules to cyclically displace at least one of the first and second bonding modules relative to the other during a bonding operation of the apparatus.

27. The apparatus of claim 26, wherein the camming device includes a rotary cam wheel mounted to the anvil module frame.

28. The apparatus of claim 26, further comprising a first motor to which the ultrasonic horn is rotatably connected, a second motor to which the anvil module is rotatably connected, and a servomotor to which the cam wheel is rotatably connected.

29. The apparatus of claim 1, wherein
the first bonding module is mounted to a first bonding module frame;
the second bonding module is mounted to a second bonding module frame and positionable in close proximity to the first bonding module; and the apparatus further comprising
a pinching device mounted to one of the first and second bonding module frame such that the pinching device is positionable to floatingly contact the second bonding module.

30. The apparatus of claim 29, wherein the pinching device includes a roller that floatingly contacts the anvil module.

31. The apparatus of claim 30, wherein the pinching device includes a base and a biasing element by which the roller is floatingly mounted to the base.

32. The apparatus of claim 29, wherein the pinching device is adjustable in at least two degrees of freedom.

33. The apparatus of claim 1, wherein the first bonding module comprises a rotary ultrasonic horn.

34. The apparatus of claim 33, wherein the second bonding module comprises a rotary anvil.

35. The apparatus of claim 26, wherein the bonding module comprises a rotary ultrasonic horn mounted to the bonding module frame.

36. The apparatus of claim 29, wherein the bonding module comprises a rotary ultrasonic horn mounted to the bonding module frame.

37. A system for fabricating an elastic nonwoven material, said system comprising:
a supply station comprising:
a first supply roll configured to supply a first nonwoven fabric;
a second supply roll configured to supply a second nonwoven fabric; and
at least one supply spool configured to supply an elastic strand;
a processing station comprising:
a first bonding module; and
a second bonding module configured to cooperate with the first bonding module to perform a bonding operation of the elastic strand between the first and second nonwoven fabrics, the second bonding module positionable in close proximity to the first bonding module, wherein one of the first bonding module and the second bonding module has a face with a width and a circumferential axis, the face having a plurality of ridges each of which defines a plurality of interspaced lands and notches, the notches oriented substantially parallel to the circumferential axis.

38. A system for fabricating an elastic nonwoven material, said system comprising:
- a processing station comprising:
  - a first bonding module; and
  - a second bonding module configured to cooperate with the first bonding module to perform a bonding operation of an elastic strand between a first nonwoven fabric and a second nonwoven fabric to fabricate the elastic nonwoven material, the second bonding module positionable in close proximity to the first bonding module, wherein one of the first bonding module and the second bonding module has a face with a width and a circumferential axis, the face having a plurality of ridges each of which defines a plurality of interspaced lands and notches, the notches oriented substantially parallel to the circumferential axis; and
- a collection station comprising a puller roll configured to collect the elastic nonwoven material.

\* \* \* \* \*